US00PP20510P3

(12) United States Plant Patent
Egger

(10) Patent No.: US PP20,510 P3
(45) Date of Patent: Dec. 1, 2009

(54) ***AGASTACHE* PLANT NAMED 'SUMMER LOVE'**

(50) Latin Name: ***Agastache* sp.**
Varietal Denomination: Summer Love

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 30 days.

(21) Appl. No.: 12/150,186

(22) Filed: Apr. 25, 2008

(65) Prior Publication Data

US 2009/0271901 P1 Oct. 29, 2009

(51) Int. Cl.
*A01H 5/00* (2006.01)

(52) U.S. Cl. ..... Plt./399

(58) Field of Classification Search ..... Plt./263, Plt./399

See application file for complete search history.

*Primary Examiner*—Annette H. Para
*Assistant Examiner*—Susan B McCormick Ewoldt
(74) *Attorney, Agent, or Firm*—Klarquist Sparkman, LLP

(57) ABSTRACT

A new and distinct form of *Agastache* plant characterized by large, vivid purple flowers in large clusters, long bloom time, upright plant habit with dense branching, and excellent vigor.

1 Drawing Sheet

Botanical denomination: *Agastache* sp.
Variety designation: 'Summer Love'.

BACKGROUND OF THE INVENTION

The present invention relates to a new and distinct cultivar of *Agastache*, given the name, 'Summer Love'. *Agastache* is in the family Lamiaceae. The new cultivar is a F2 selection from a planned breeding program. The original cross was between a dwarf form of *Agastache pallidiflora* 'Pink Pop' (an unpatented plant) as the seed parent and a dark pink *Agastache cana* (an unpatented plant) as the pollen parent.

This plant exhibits the following characteristics:

1. Large, vivid purple flowers in large clusters,
2. Upright plant habit with dense branching,
3. Long bloom time,
4. Excellent vigor.

The new variety has been reproduced only by asexual propagation (cuttings and micropropagation). Each of the progeny exhibits identical characteristics to the original plant. Asexual propagation by division and micropropagation as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The drawing shows a one-year-old *Agastache* 'Summer Love' growing in the garden in late summer in Canby, Oreg.

DETAILED PLANT DESCRIPTION

The following is a detailed description of the new *Agastache* cultivar based on observations of two-year-old specimen grown outside in the ground in the garden in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart.

Plant:

*Form.*—Upright, herbaceous perennial.
*Cold hardiness.*—USDA Zone 6–9.
*Size.*—Grows to 90 cm tall and 60 cm wide.
*Vigor.*—Excellent.
*Stem.*—Square, grows to 8 mm wide and 60 cm tall, internodes average 6 cm long, Yellow Green 147B, with lateral branching at each node.
*Roots.*—White 155B, fibrous, plants root easily from stem tip cuttings.

Leaf:

*Type.*—Simple.
*Arrangement.*—Opposite.
*Shape.*—Ovate.
*Venation.*—Pinnate.
*Margins.*—Crenate.
*Apex.*—Obtuse.
*Base.*—Cordate.
*Blade size.*—Grows to 4.2 cm long and 2.4 cm wide.
*Surface texture.*—Puberulous on both sides.
*Petiole description.*—Grows from 2.6 cm long to 0.9 cm long and 1.4 mm wide, puberulous, Yellow Green 147C.
*Leaf color.*—Top side — closest to Yellow Green 147A, but darker. Bottom side — Yellow Green 147B.

Inflorescence:

*Type.*—Terminal spike.
*Number of flowers.*—About 190 per spike in 9 to 25 flowered, dense whorls.
*Peduncle.*—20 cm to 30 cm tall and 2 mm wide, pubescent, Yellow Green 147B.
*Pedicel.*—1 mm to 4 mm long, pubescent, color closest to Greyed Orange 177A, but more purple.
*Bloom period.*—June through frost in Canby, Oreg.

Flower bud:

*Size.*—17 mm long and 3 mm wide at the widest point prior to opening.

*Description.*—Tubular.

*Surface texture.*—Pubescent.

*Color.*—Greyed Purple 187C.

Flower:

*Type.*—Zygomorphic.

*Shape.*—Bilabiate, tubular.

*Size.*—3 cm long and 1 cm wide.

*Corolla description.*—3 cm long and spreads to 1 cm wide, color Red Purple 72A inside and out, pubescent inside and out, tube 2.3 cm long and 1 mm to 4 mm wide, 2 upper lobes joined 3 mm long and 4 mm wide, acute, entire, three lower lobes, two spreading sideways, the terminal lobe broad, reflexed, obcordate and mucronate, entire, 6 mm wide and 5 mm deep, two side lobes 3 mm long and 2.5 mm wide.

*Calyx description.*—7 mm long and 3 mm wide, color between Greyed Purple 187A and Gray 201A, pubescent outside and glabrous inside, 5 lobed, lobes narrow 3 mm long, entire, acuminate.

*Pistil description.*—36 mm long, ovary 0.5 mm long, Yellow Green 146C, style and stigma 35.5 mm long, Red Purple 72A at the tip to White 155D at base.

*Stamen description.*—4 in number, paired, exerted and reflexed, filaments 7 mm long, Red Purple 72A, anthers 1 mm long, Violet 83A, pollen White 155D.

*Fragrance.*—Strong, herbal.

*Lastingness.*—A spike blooms for about 3 weeks on the plant.

Fruit: 4 nutlets, Green 144A.

Seed: Oblong, 1.5 mm long, Black 202A, fertile.

Pests and diseases: *Agastache* are known to be susceptible to mildew and rust in dry summer months. The new cultivar has no known resistances but has shown no problems in Canby, Oreg.

Comparisons: Compared to *Agastache pallidiflora* 'Pink Pop' dwarf, the seed parent, the new variety has brighter purple flowers with darker calyces, larger flowers and inflorescences. Compared to the dark pink *Agastache cana*, the pollen parent, the new variety has denser inflorescences, with brighter, more purple, flower color, and a more compact habit. Compared to *Agastache* 'Kiegapur' (US Plant Pat. No. 16,067), the new variety has darker purple flowers and a taller, denser habit. Compared to *Agastache* 'Raspberry Summer' (U.S. Plant patent application Ser. No. 12/150,185), the new variety is taller with vivid purple flowers rather than purple red flowers.

I claim:

1. A new and distinct form of *Agastache* plant substantially as shown and described.

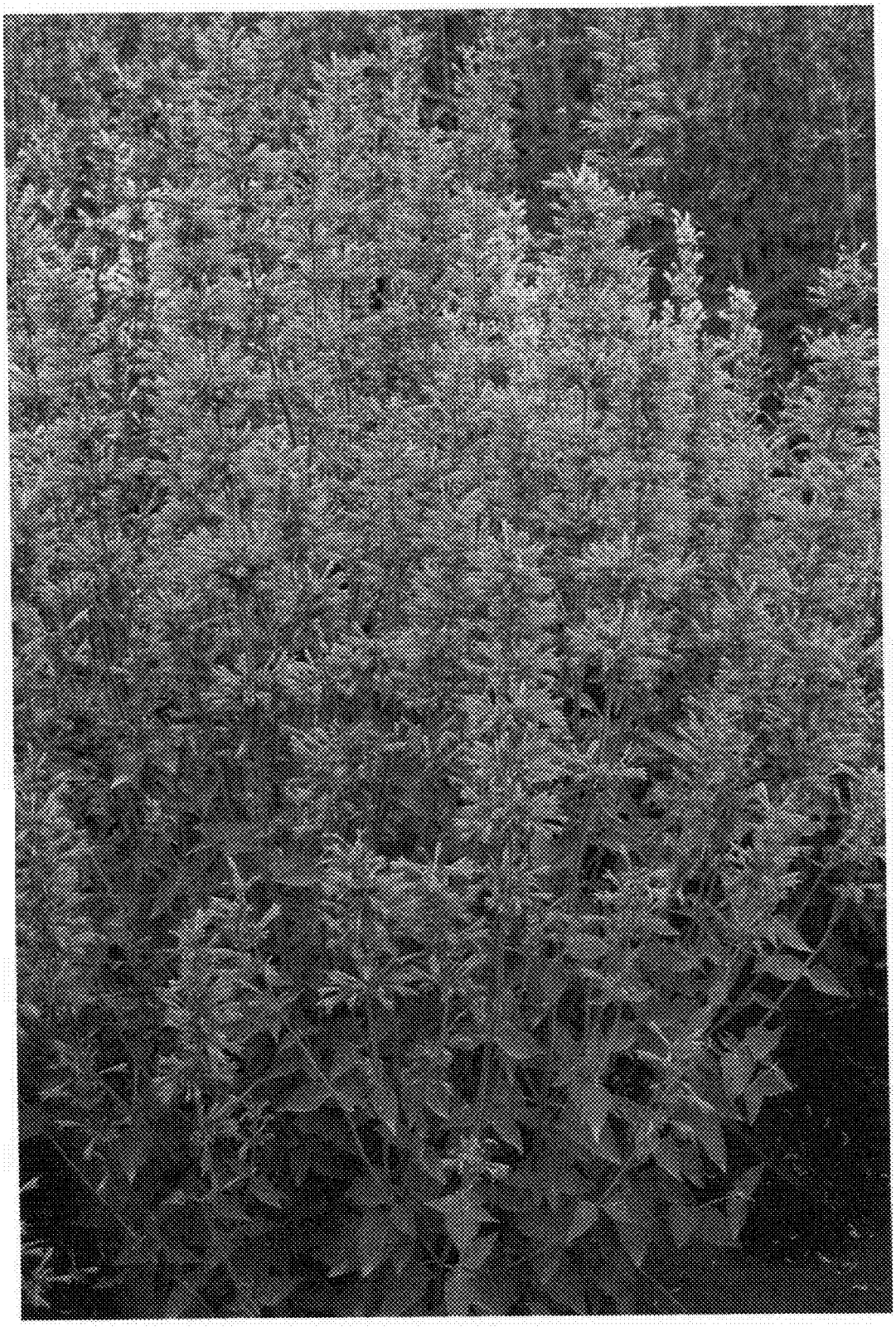

* * * * *